United States Patent [19]
Meyer

[11] Patent Number: 5,779,472
[45] Date of Patent: Jul. 14, 1998

[54] TESTING OF USEFUL DENTAL VACCUM

[75] Inventor: Robert A. Meyer, Spearfish, S. Dak.

[73] Assignee: RAMVAC Corporation, Spearfish, S. Dak.

[21] Appl. No.: 390,977

[22] Filed: Feb. 21, 1995

[51] Int. Cl.⁶ .............................. A61C 17/06; A61C 17/14
[52] U.S. Cl. .................................................. 433/91
[58] Field of Search .................. 433/91, 92, 93, 433/94, 95, 96; 73/168

[56] References Cited

U.S. PATENT DOCUMENTS

| | | | |
|---|---|---|---|
| 5,044,953 | 9/1991 | Sullivan | 433/91 X |
| 5,263,860 | 11/1993 | Shen et al. | 433/91 |

*Primary Examiner*—Nicholas D. Lucchesi
*Attorney, Agent, or Firm*—Nixon & Vanderhye P.C.

[57] ABSTRACT

A method and apparatus provide for testing the useful vacuum of a dental vacuum system having at least one high volume evacuator valve (HVE) or hose. The vacuum tester is simple, inexpensive, can be used by non-technical personnel, is easily fabricated to test a wide range of performance standards, and evaluates useful vacuum performance during full flow (that is a real-life situation). The tester includes two simple components, an adaptor tube that is placed into contact with an HVE or hose, and a vacuum indicating weight which cooperates with the adaptor tube. With the dental vacuum system operating the weight is brought into position with respect to the tube so that gravity acts to move the weight away from the tube, and then the weight is released. If the weight moves away from the tube the useful vacuum conditions of the dental vacuum system are insufficient, whereas if the weight stays in operative position with respect to the tube the useful vacuum conditions are sufficient. The tube and the weight can each have a wide variety of configurations, and the weight can have an adjustable mass and/or internal cross-sectional configuration.

19 Claims, 3 Drawing Sheets

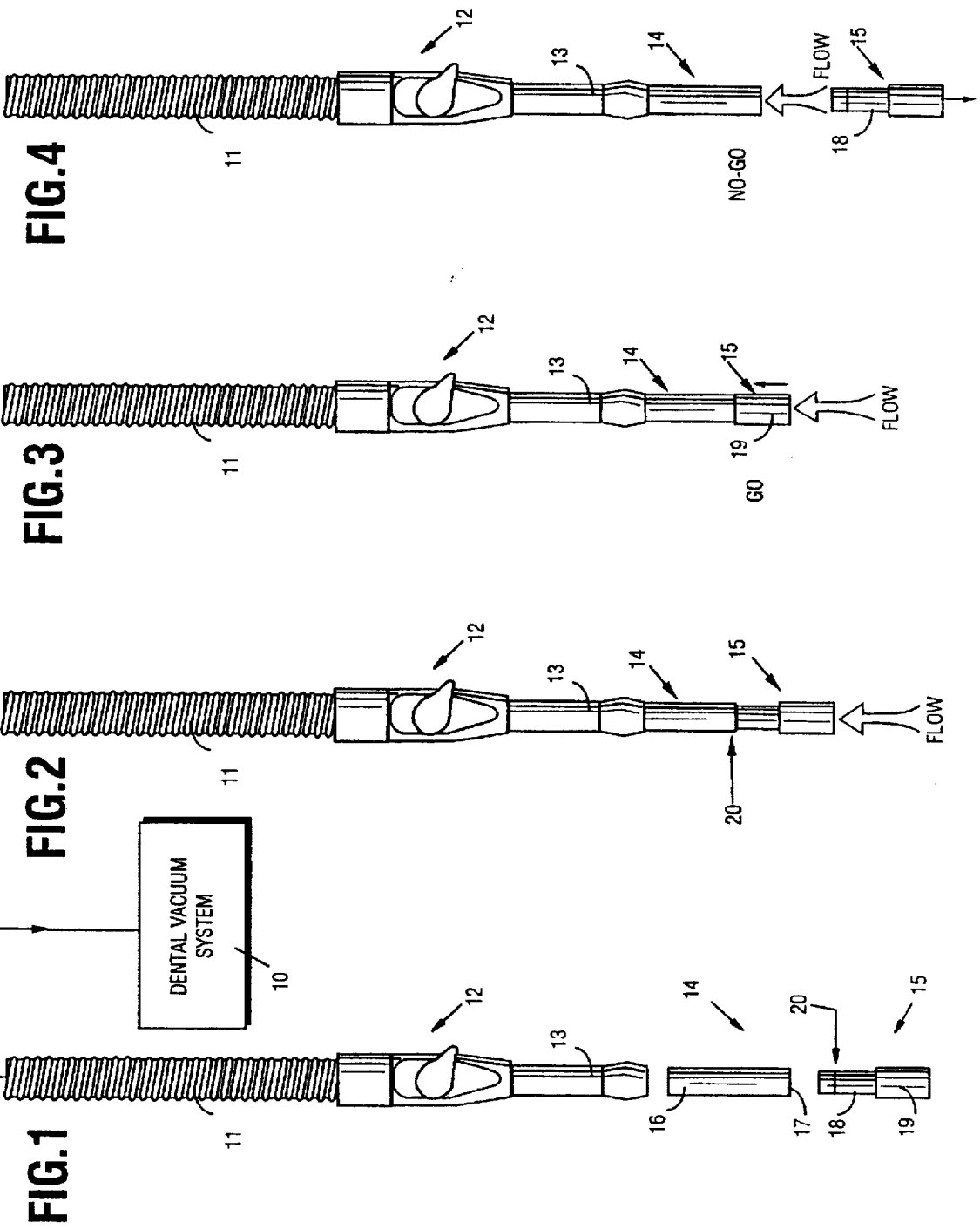

TESTING OF USEFUL DENTAL VACCUM

BACKGROUND AND SUMMARY OF THE INVENTION

A dental vacuum is used to remove a wide variety of materials from the operating field in a dental treatment room. A successful conventional dental vacuum system is shown in U.S. Pat. No. 5,282,744 (the disclosure of which is hereby incorporated by reference herein). The vacuum drawn by the dental vacuum system is useful only when the materials are actually being moved. Static vacuum provides no function and is not useful vacuum. The vacuum intensity available at the point of use during full flow determines a dental vacuum system's useful capacity and capability.

In order to successfully test useful vacuum system performance in dental vacuum systems, vacuum intensity and flow must be tested in the treatment room. Particularly high volume evacuator (HVE) valves and hoses must be evaluated. While flow meters can evaluate flow, they are expensive and require significant technical knowledge to be used effectively. Pressure measuring devices, such as vacuum gages, partially or completely obstruct flow and therefore do not test useful vacuum performance. Therefore a method and apparatus are needed which can in a simple and inexpensive manner effectively test the useful vacuum performance for dental vacuum systems.

According to the present invention a method and apparatus are provided which are simple, inexpensive, and can be utilized or practiced without training by non-technical personnel. According to the invention useful vacuum performance is tested during full flow conditions, and the apparatus of the invention can be fabricated in a number of different ways to test a wide range of performance standards, but is particularly useful for testing to ensure that the vacuum performance is greater than about 7.25 SCFM and about 4.6 inches of mercury.

According to one aspect of the present invention a method of testing the useful vacuum of a dental vacuum system during full flow is provided. The system has at least one HVE valve or at least one hose, and the method uses an adaptor tube and a vacuum indicating weight. The method comprises the steps of: (a) Placing the adaptor tube into contact with an HVE valve or a hose of the dental vacuum system so that air is drawn by the dental vacuum system through the adaptor tube into the HVE valve or hose when the dental vacuum system is operating. (b) With the dental vacuum system operating, bringing the vacuum indicating weight into position with the adaptor tube so that gravity acts to move the vacuum indicating weight away from the adaptor tube, while positioning the adaptor tube so that it is substantially vertical and the high volume evacuator valve or hose is substantially above the adaptor tube. And, (c) after step (b), releasing the vacuum indicating weight, the weight moving away from the adaptor tube indicating that the dental vacuum system has insufficient useful vacuum conditions, and the weight staying in position with the adaptor tube indicating that the dental vacuum system has sufficient useful vacuum conditions. For example steps (a) through (c) may be practiced so that if the weight moves away from the adaptor tube that indicates that the dental vacuum system has useful vacuum conditions of less than about 7.25 SCFM and 4.6 inches Hg, and if the weight stays in position with the adaptor tube that indicates that the dental vacuum system useful vacuum conditions are greater than about 7.25 SCFM and 4.6 inches Hg.

The vacuum indicating weight may be tubular and have a first portion with a first outside diameter which fits within an open end of the adaptor tube so that air flow between the exterior of the first portion and the adaptor tube is substantially precluded but there is no interference fit between the vacuum indicating weight and the adaptor tube, and the vacuum indicating weight has a second portion with an outside diameter greater than that of the first portion and which will not fit within the adaptor tube. In that case step (b) is practiced by moving the vacuum indicating weight first portion into the adaptor tube open end so that air flows through the vacuum indicating weight into the adaptor tube, and step (c) is practiced by releasing the vacuum indicating weight when the first portion is in the adaptor tube. The first portion of the vacuum indicating weight may have external indicia (e.g. a "start" line) thereon indicating the amount of insertion thereof into the adaptor tube. In that case step (b) is further practiced by inserting the first portion into the adaptor tube up to the external indicia thereon.

The vacuum indicating weight may have a calibration element which modifies the mass or internal cross-section thereof. In that case there is the further step of (d) adjusting the position of the calibration element with respect to the tubular vacuum indicating weight to modify the amount of useful dental vacuum necessary to hold the tubular vacuum indicating weight in position with respect to the adaptor tube in the practice of step (c). If the calibration element is a calibration screw then step (d) is practiced by rotating the screw to adjust its position with respect to the internal cross-section of the tubular vacuum indicating weight. Calibration may be performed by the operator at the time of testing, or if a user of the invention specifies very tight specifications to the factory, the calibration can be done at the factory by adjusting the calibration screw, and the screw acted upon at the factory to hold it in the place to which it has been adjusted in the weight.

Alternatively the adaptor tube may have an elongated surface extending outwardly from the HVE valve or hose with at least one opening therein, and the vacuum indicating weight may be a structure which can be mounted to cover or move away from the adaptor tube elongated surface opening. In that case step (b) is practiced by covering the at least one opening in the adaptor tube elongated surface with the vacuum indicating weight; and step (c) is practiced by releasing the vacuum indicating weight when it covers the at least one opening in the adaptor tube elongated surface.

According to another aspect of the present invention a simple yet effective "Go", "No-Go" vacuum tester is provided comprising the following elements: An adaptor tube having open first and second ends, a constant cross-sectional area and configuration interior surface portion adjacent a second end thereof, and an external surface at at least the first end adapted to fit tightly with a valve or hose. And, a tubular vacuum indicating weight having: a first portion with an exterior cross-section dimensioned and configured so that it fits within the adaptor tube open second end in association with the adaptor tube interior surface so that airflow between the exterior cross section of the first portion and the adaptor tube interior surface is substantially precluded but there is no interference fit therebetween; a second portion with an exterior cross-section greater than that of the first portion and which will not fit within the adaptor tube open second end; and an internal passageway.

The first portion of the vacuum indicating weight may have external indicia (a "Start" line) thereon indicating the desired amount of insertion thereof into the adaptor tube open second end. Also it may have a calibration element which modifies the weight or internal cross-section thereof, such as a calibration screw movable into and out of the internal passageway. Typically the adaptor tube is made of plastic while the vacuum indicating weight is of stainless steel. Where the "Go", "No-Go" specifications are approximately 7.25 SCFM and 4.6" Hg, the adaptor tube has a substantially circular cross-section internal surface having a diameter of about 0.4 inches, an external circular surface with a diameter of about 0.42–0.44 inches at the first end thereof, and the vacuum indicating weight has a first portion exterior with a substantially circular cross-section and an external diameter of about 0.35–0.36 inches and the vacuum indicating weight has a mass of about 23 grams.

According to another aspect of the present invention a dental vacuum system assembly is provided comprising the following elements: A dental vacuum system for drawing a vacuum useful for dental purposes. At least one dental vacuum system high volume evacuator valve or hose connected to the dental vacuum system so that air is drawn into the valve or hose. An adaptor tube having a first open end and a second end, a constant cross-sectional area and configuration interior surface, and an external surface at at least the first end tightly fit with the dental vacuum system high volume evacuator valve or hose, and having a testing opening. And, a vacuum indicating weight movably positioned to cooperate with the testing opening, the weight configured and dimensioned to, once moved into a position cooperating with the testing opening, remain in a position cooperating with the testing opening when the useful vacuum drawn by the vacuum system is at or above a level considered sufficient, and move away from the testing opening when the useful vacuum drawn by the vacuum system is at or below a level considered insufficient.

A wide variety of modifications may be provided. For example the testing opening may comprise at least one opening in the external surface of the adaptor tube through which air flow from exterior of the adaptor tube through the testing opening and then through the first open end may be provided, and the vacuum indicating weight may comprise a portion which is mounted for movement between a first position covering the at least one opening and a second position not covering the opening. For example the vacuum indicating weight may comprise a tube which slides over the external surface of the adaptor tube, or an element that is pivoted to the adaptor tube.

Alternatively the adaptor tube second end may be open and the vacuum indicating weight may be solid (e.g. a metal sphere or cone) and dimensioned to completely cover the adaptor tube second open end, air flow being provided through the at least one opening in the external surface during the testing under full flow conditions.

Still further, the adaptor tube and the vacuum indicating tube of the dental vacuum system assembly may be as described above, i.e. where the vacuum indicating weight is tubular and is inserted into the open second end of the adaptor tube.

It is the primary object of the present invention to provide for the simple, inexpensive, and accurate evaluation of useful vacuum performance during full flow of dental vacuum systems. This and other objects of the invention will become clear from an inspection of the detailed description of the invention, and from the appended claims.

BRIEF DESCRIPTION OF THE DRAWINGS

FIGS. 1 through 4 are successive schematic views illustrating dental vacuum system useful vacuum testing according to the present invention;

DETAILED DESCRIPTION OF THE DRAWINGS

Figure 8:
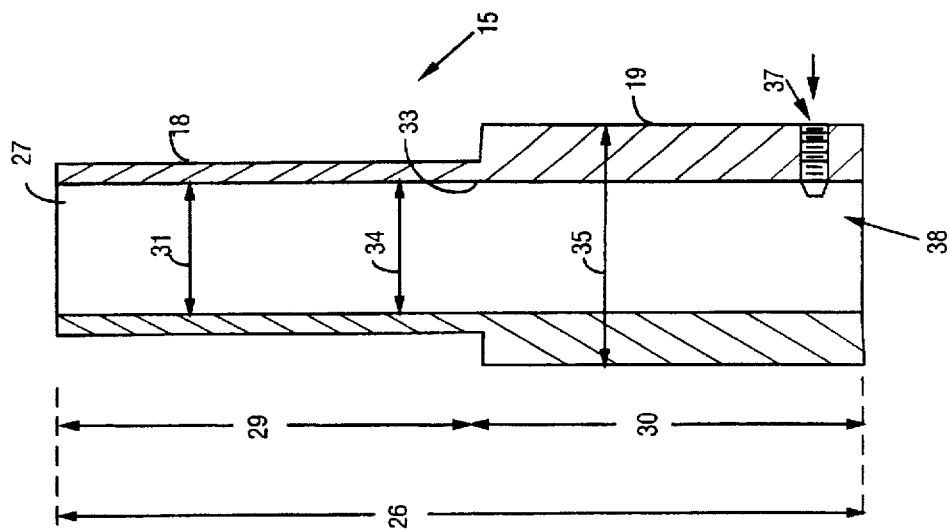
FIGS. 7 and 8 are side elevational and cross-sectional views, respectively, of two different modifications of vacuum indicating weights used in the practice of the procedure illustrated in FIGS. 1 through 4.

FIGS. 1 through 4 schematically illustrate the practice of a method of testing the useful vacuum of a dental vacuum system, during full flow, according to the present invention. The dental vacuum system is shown schematically at 10 in FIG. 1 and may be of any conventional type, such as shown in U.S. Pat. No. 5,282,744. In the actual operating field a dental vacuum assembly which includes the dental vacuum system 10 typically has a hose 11 and a high volume evacuator (HVE) valve 12. In fact normally a number of hoses 11 and HVE valves 12 will be associated with the system 10. The valve 12 includes an extension 13 adapted to connect it to a variety of different types of equipment or structures.

According to the method of the present invention vacuum testing is accomplished utilizing only two simple structures, an adaptor tube, shown generally by reference numeral 14, and a vacuum indicating weight, shown generally by reference numeral 15. For the embodiment illustrated in FIGS. 1 through 4 the tube 14 has first and second open ends 16, 17 respectively, the open end 16 normally being adapted to be inserted into the extension 13 of the HVE valve 12, only also possibly being constructed (depending upon its length, the vacuum performance to be evaluated, etc.) so that it fits over the extension 13 or it is otherwise affixed to it. The adaptor tube 14 provides a significant known constant cross-sectional area (typically circular, having a diameter) so that testing will be accurate. The length of the known constant cross-sectional area is required to be only just enough to receive a portion of the vacuum indicating weight element 15 therein (as described below).

In the FIGS. 1 through 4 embodiment the vacuum indicating weight 15 is also tubular, having a first portion 18 dimensioned so that it will fit within the open second end 17 of the adaptor tube 14, and a second portion 19 which will not fit within the open end 17. Indicia, typically in the form of a "Start" line 20, may be provided on the portion 18. The weight 15 has a known mass and internal cross-section which are calibrated for the particular vacuum performance characteristics to be evaluated (flow rate typically in standard cubic feet per minute (SCFM) and vacuum intensity, typically in inches of mercury).

A preferred method, as illustrated in FIGS. 1 through 4, according to the invention, is to insert the adaptor tube 14 first open end 16 into the extension 13 of the HVE valve 12, with the system 10 operating or not operating. Then—if they are not already in that position—the hose 11 and valve 12 are positioned so that they are substantially vertical, and above the adaptor tube 13. Then the vacuum system 10 is operated (full flow), if not already on, and the weight 15 first portion 18 is inserted into the second open end 17 of the adaptor tube 14 up to the Start line 20—as illustrated in FIG. 2. The typically non-technical person doing the vacuum testing after moving the weight 15 into the position illustrated in FIG. 2, and while maintaining the hose and valve 12 substantially vertical and above the tube 14 and weight 15, releases the weight 15 so that gravity acts on the weight 15. If the vacuum conditions are sufficient (e.g. a flow of at least about 7.25 SCFM and a vacuum intensity of at least about 4.6 inches Hg) then the weight 15 will stay with the portion 18 thereof within the tube 14. The weight 15 thus will either be maintained in the position illustrated in FIG. 2, or if the vacuum is sufficient will actually be pulled further into the tube 14 up to the second portion 19, as illustrated in FIG. 3, which shows a typical "Go" position. As illustrated in FIGS. 2 and 3 during this time air is flowing through the tubular weight 15 ultimately to the dental vacuum system 10.

If the dental vacuum system 10 has insufficient useful vacuum conditions (that is flow and vacuum intensity in the operating field) then the weight 15 will, under the force of gravity, fall out of operative association with the adaptor tube 14, as indicated in FIG. 4. For example if the useful vacuum conditions are less than about 7.25 SCFM and 4.6" Hg the weight 15 will fall away under the force of gravity as illustrated in FIG. 4. This is the "No-Go" condition.

While typically the adaptor tube 14 is a separate element from the valve 12 or hose 11, depending upon the particular dental office it may be possible to actually construct the valve 12 or hose 11 having a built in adaptor like the adaptor tube 14 to accommodate the weight 15, and this is also within the scope of the invention.

In the practice of methods according to the present invention, normally testing would be done for a system with multiple vacuum devices in simultaneous use. That is the operating condition under which the performance of system 10 is evaluated would be created by turning on the required number of HVEs, saliva ejectors, surgical suctions, nitrous oxide scavengers, and the like, and then selecting one open HVE, or hose, as the test site.

The method of the invention also may be used to identify substandard vacuum system performance that may exist at one or some HVE valve or hose locations. For example, one might wish to test the performance at each HVE valve in a four treatment room facility with HVE valves in two other rooms open. In such a procedure, the HVE valve in the first room would be tested while the HVE valves in the second and third rooms were open, then the HVE valve in the second room with the HVE valves in the first and fourth rooms open, etc. This may indicate "go" in some rooms, and "no-go" in others, indicating local obstructions in piping or specific treatment room vacuum components that they could be isolated and cured.

FIGS. 5 through 8 illustrate exemplary particular details of the adaptor tube (14) and vacuum indicating weight (15) that may be utilized according to the invention. The dimensions described with respect to FIGS. 5 through 8 are for testing vacuum performance which will be "Go" if above about 7.25 SCFM and 4.6" Hg, or "No-Go" if less than that.

Figure 6:
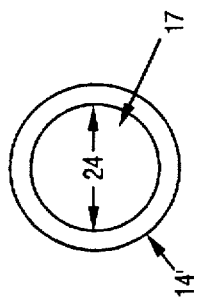
FIG. 6 is a bottom plan view of the adaptor tube of FIG. 5.
Figure 5:
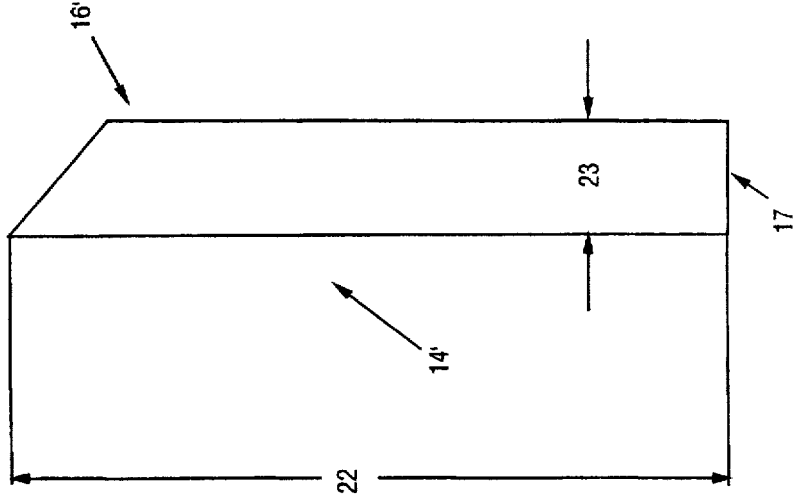
FIG. 5 is a detail side view of one form the adaptor tube used in the procedure illustrated in FIGS. 1 through 4 may take.

The adaptor tube 14' illustrated in FIGS. 5 and 6 is the same as the adaptor tube 14 only the first end 16' thereof has a bevel cut. The tube 14' has a length 22 of about three to four inches, e.g. about 3¼ inches±⅛ inch. The tube 14' preferably is circular in cross-section (has both inside and outside diameters). The outside diameter 23 (see FIG. 5) is preferably about 0.42–0.44 inches (at least at the first end 16' thereof), e.g. 0.433 inches±0.01 inches. The inside diameter 24 (see FIG. 6), which is preferably completely uniform throughout the entire length 22, is typically about 0.4 inches, e.g. 0.395 inches+0.005 inches,–0.01 inches. It is possible to make the inside diameter 24 uniform at only that portion thereof adjacent second end 17, with a length that is long enough to properly receive lo the entire weight first portion 18 therein. The adaptor tube 14' typically is made of a hard plastic material, although it can be made of almost any material that will maintain its configuration.

Figure 7:
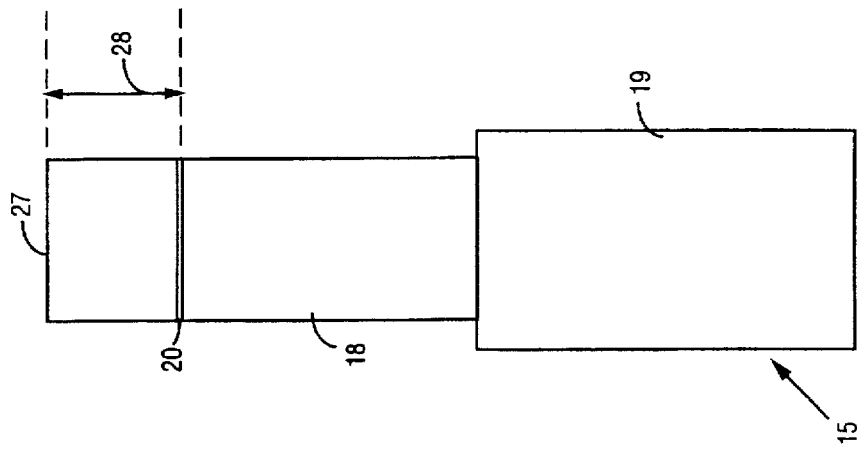

The vacuum indicating weight 15 is illustrated in detail in FIGS. 7 and 8. Its total length 26 (see FIG. 8) is typically about 1.75–2 inches, preferably about 1⅞ inch±0.01 inches. The "Start" line 20, or other indicia indicating the desired amount of insertion, is parallel to the first open end 27 thereof and spaced a distance 28 thereof, the distance 28 being typically about 5/16 of an inch (e.g. 5/16±0.01 inches). Both the portions 18 and 19 are preferably circular in cross-section, both internally and externally. The length 29 (see FIG. 8) of the first portion 18 may, for example, be about 1 1/16 inch (e.g. ±0.01 inches), while the length 30 of the second portion 19 is about 13/16 of an inch (e.g. ±0.01 inches).

The external (outside) diameter 31 (see FIG. 8) of the first portion 18 is small enough to fit within the second open end 17 of the adaptor tube 14, 14', without making an interference fit therewith, but is large enough so that air flow between the external diameter of the portion 18 and the tube 14, 14' is substantially precluded (that is so that the vast majority of the air flow is through the internal circular cross-section passageway 33 in the weight 15). For example the diameter 31 may be about 0.35–0.36 inches (e.g. about 0.355 inches±0.004 inches). The internal diameter 34 typically is about 0.24 inches, e.g. about 0.234 inches+0.008 inches,–0.000 inches. The internal diameter 34 is uniform through the entire length 26, but the external diameter 35 of the second portion 19 is greater than the internal diameter 24 of the adaptor tube 14', the diameter 35 typically being about ½ inch (e.g. 0.5 inches±0.004 inches).

The vacuum indicating weight 15 is preferably made of a material which is sufficiently massive and dense so that it need not be too large as to be unwieldy. Given the dimensions described above the weight 15 is made of 416 stainless steel, and it has a mass of about 23 grams (e.g. 23.1±0.2 grams).

The dimensions and configurations of the elements 14, 14', and 15 may be modified so as to be able to evaluate a wide variety of is different performance conditions. Inherent adjustability can be provided within the weight 15 itself, if desired, by using a calibration element. The calibration element may be of a wide variety of types, such as inserts, external magnets, collars, or the like, which are capable of modifying either the mass or the internal cross-section (shape or dimensions) 34 of the vacuum indicating weight 15. A simple, preferred calibration element is—as seen in FIG. 8—a calibration screw 37. For example the screw 37 may be a #4-40×3/16 inch set screw positioned about 3/16 of an inch from the open second end 38 of the weight 15, the set screw 37 being movable into and out of the passage 33 to modify its internal cross-section and thus the vacuum conditions which result in the "Go" and "No-Go" conditions of FIGS. 3 and 4. Also the screw 37 may be removed from the weight 15 completely by unscrewing it, which changes the mass of the vacuum indicating weight 15.

Figure 11:
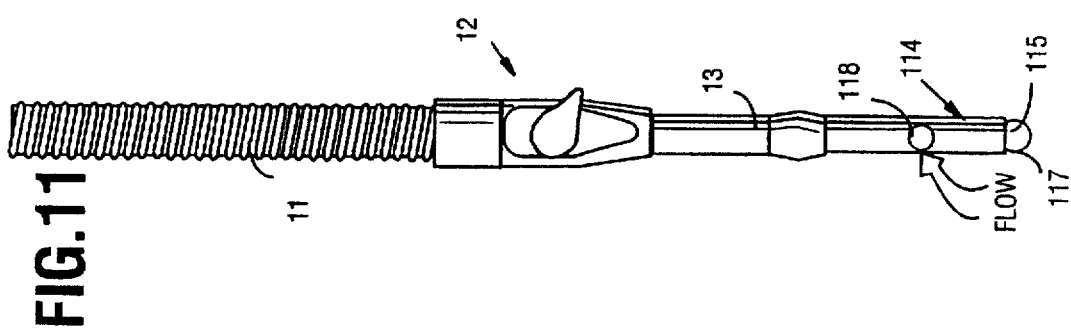
FIGS. 9 through 11 are views like those of FIGS. 1 through 4 only showing a procedure of dental vacuum testing utilizing different configurations of the adaptor tube and vacuum indicating weight.
Figure 10:
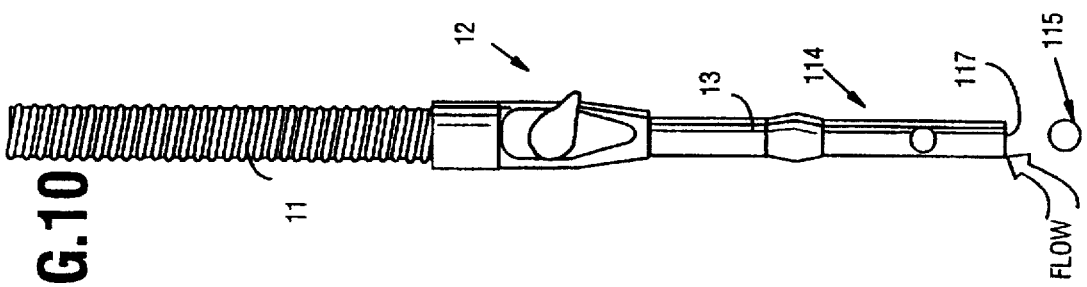
Figure 9:
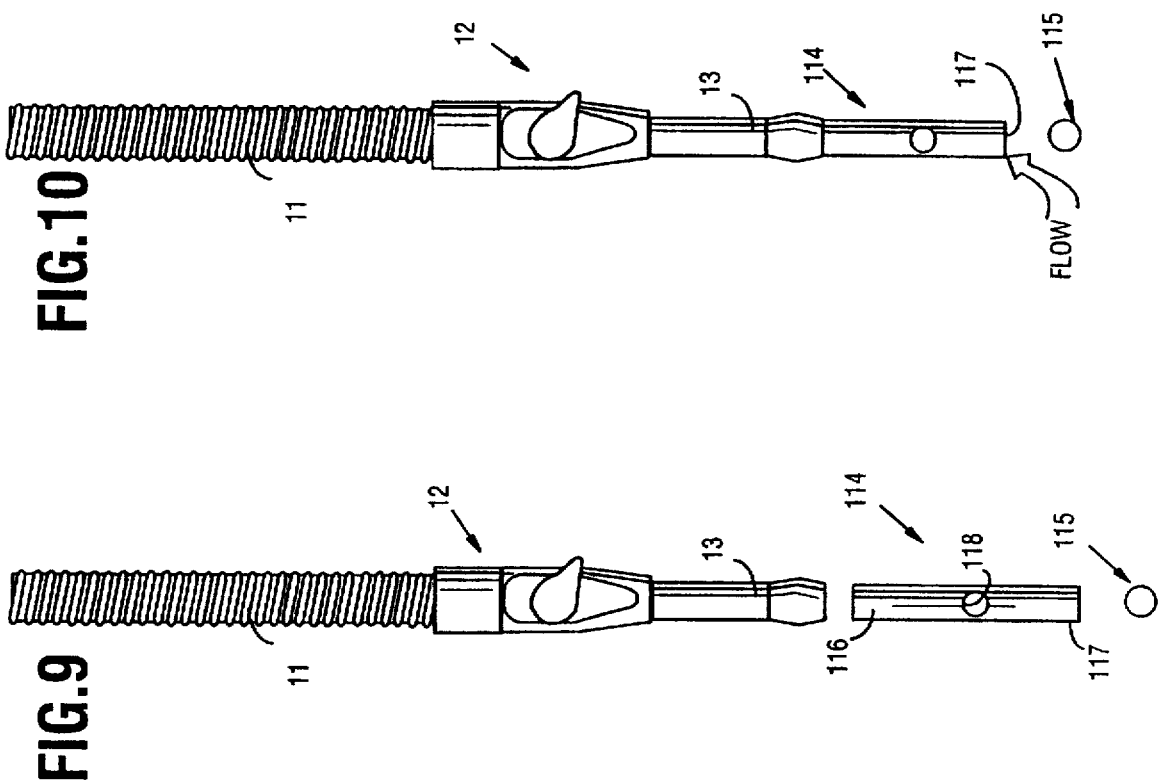

Although the construction of the adaptor tube 14, 14' and vacuum indicating weight 15 illustrated in FIGS. 1 through 8 is particularly desirable, a wide variety of other configurations may also be provided. For example FIGS. 9 through 11 illustrate different configurations of an adaptor tube 114 and a vacuum indicating weight 115. In FIGS. 9 through 11 the elements 11 through 13 are the same as in FIGS. 1 through 4, and are positioned in the same way during testing.

As seen in FIGS. 9 through 11 the adaptor tube 114 has first and second open ends 116, 117, but also has an opening (i.e. at least one opening) 118 in the external surface thereof. The weight 115 is a solid structure, in the embodiment actually illustrated in FIGS. 9 through 11 a stainless steel sphere (e.g. a ball bearing) having a diameter larger than the internal diameter of the second open end 117 of the adaptor tube 114. The element 115 could alternatively be cup-shaped, conical, or have other shapes.

As illustrated in FIG. 10, after the adaptor tube 114 is inserted into the extension 13 of the HVE valve 12 the ball 115 is moved toward the open end 117 of the tube 114. As seen in FIG. 11 if the useful vacuum conditions are sufficient the ball 115 will be held in place occluding the open end 117 while air flows through the opening 118 ultimately to the hose 11 and vacuum system 10. Although not in the drawings, the "No-Go" position will be where the ball 115 falls away from the adaptor tube 114 because the useful vacuum conditions are insufficient.

Figure 12:
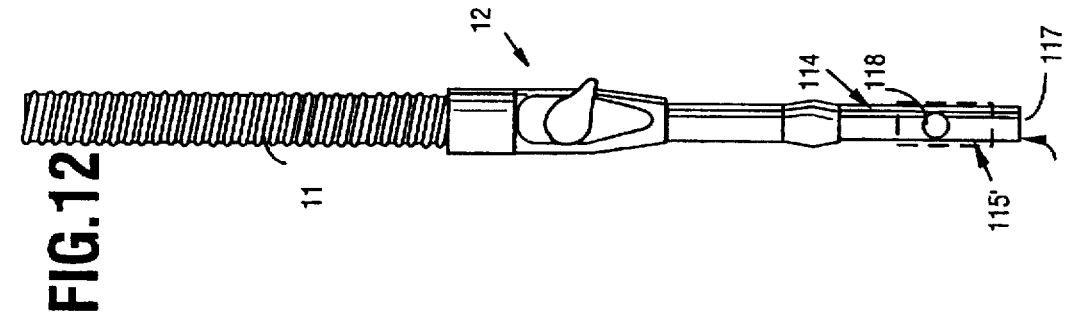
FIG. 12 is a view like that of FIG. 11 only showing a still different configuration of vacuum indicating weight.

Yet another embodiment similar to that of FIGS. 9 through 11 is illustrated in FIG. 12. In this embodiment the adaptor tube 114 is the same including the opening 118 therein, but in this embodiment the weight 115' is in the form of a tube (shown in dotted line in FIG. 12) having an internal diameter slightly greater than the external diameter of the adaptor tube 114 so that the weight tube 115' can slide over the exterior surface of the adaptor tube 114. The weight tube 115' is placed in a position covering the opening 118, and if the vacuum system has sufficient useful vacuum conditions the weight tube 115' will remain in place (as illustrated in dotted line in FIG. 12). If the system 10 has insufficient useful vacuum conditions, the weight tube 115' will drop off the adaptor tube 114.

Other embodiments are also possible. For example the vacuum indicating weight may be pivoted to the tube 114 selectively covering or uncovering the opening 118, the vacuum indicating weight may be pivotally mounted to the bottom of the tube 14 and the components held slightly off vertical during testing, or a wide variety of other modifications are possible. In any event the present invention clearly is provides a simple and inexpensive, yet accurate, testing device and method for testing useful vacuum in dental treatment systems under full flow conditions, the invention being so easy to practice and utilize that untrained non-technical personnel may practice it. The invention is also very versatile, allowing components to be fabricated to test a wide variety of performance standards. For example in the same kit with a single adaptor tube 14 a number of different weights 15 may be provided instead of, or in addition to, a weight with a calibration screw 37.

Calibration may be performed by the operator at the time of testing (e. g. as in FIGS. 1–4), or if a user of the invention specifies very tight specifications to the factory, the calibration can be done at the factory by adjusting the calibration screw 37, and the screw 37 acted upon at the factory to hold it in the place to which it has been adjusted in the weight.

While the invention has been herein shown and described in what is presently conceived to be the most practical and preferred embodiment thereof it will be apparent to those of ordinary skill in the art that many modifications may be made thereof within the scope of the invention, which scope is to be accorded the broadest interpretation of the appended claims so as to encompass all equivalent methods and apparatus.

What is claimed is:

1. A method of testing the useful vacuum of a dental vacuum system, during full flow, the system having at least one high volume evacuator valve or at least one hose, using an adaptor tube and a vacuum indicating weight, comprising the steps of:
   (a) placing the adaptor tube into contact with a high volume evacuator valve or a hose of the dental vacuum system so that air is drawn by the dental vacuum system through the adaptor tube into the high volume evacuator valve or hose when the dental vacuum system is operating;
   (b) with the dental vacuum system operating, bringing the vacuum indicating weight into position with the adaptor tube so that gravity acts to move the vacuum indicating weight away from the adaptor tube, while positioning the adaptor tube so that it is substantially vertical and the high volume evacuator valve or hose is substantially above the adaptor tube; and
   (c) after step (b), releasing the vacuum indicating weight, the weight moving away from the adaptor tube indicating that the dental vacuum system has insufficient useful vacuum conditions, and the weight staying in position with the adaptor tube indicating that the dental vacuum system has sufficient useful vacuum conditions.

2. A method as recited in claim 1 wherein the vacuum indicating weight is tubular and has a first portion with a first outside diameter which fits within an open end of the adaptor tube so that airflow between the exterior of the first portion and the adaptor tube is substantially precluded but there is no interference fit between the vacuum indicating weight and the adaptor tube, and the vacuum indicating weight has a second portion with an outside diameter greater than that of the first portion and which will not fit within the adaptor tube; and wherein step (b) is practiced by moving the vacuum indicating weight first portion into the adaptor tube open end so that air flows through the vacuum indicating weight into the adaptor tube, and step (c) is practiced by releasing the vacuum indicating weight when the first portion is in the adaptor tube.

3. A method as recited in claim 2 wherein the first portion of the vacuum indicating weight has external indicia thereon indicating the amount of insertion thereof into the adaptor tube; and wherein step (b) is further practiced by inserting the first portion into the adaptor tube up to the external indicia thereon.

4. A method as recited in claim 2 wherein the tubular vacuum indicating weight has an internal cross-section, and a calibration element which modifies the mass or internal cross-section thereof; and comprising the further step of (d) adjusting the position of the calibration element with respect to the tubular vacuum indicating weight to modify the amount of useful dental vacuum necessary to hold the tubular vacuum indicating weight in position with respect to the adaptor tube in the practice of step (c).

5. A method as recited in claim 4 wherein the calibration element is a calibration screw which is movable into or out of the internal cross-section of the tubular vacuum indicating weight at the second portion thereof; and wherein step (d) is practiced by rotating the screw to adjust its position with respect to the internal cross-section of the tubular vacuum indicating weight.

6. A method as recited in claim 1 wherein the adaptor tube has an elongated surface extending outwardly from the high volume evacuator valve or hose with at least one opening therein, and wherein the vacuum indicating weight is a structure which can be mounted to cover or move away from the adaptor tube elongated surface at least one opening; and wherein step (b) is practiced by covering the at least one opening in the adaptor tube elongated surface with the vacuum indicating weight; and step (c) is practiced by releasing the vacuum indicating weight when it covers the at least one opening in the adaptor tube elongated surface.

7. A method as recited in claim 1 wherein steps (a)-(c) are practiced so that if the weight moves away from the adaptor tube that indicates that the dental vacuum system has a useful vacuum of less than about 7.25 SCFM and 4.6 inches Hg, and if the weight stays in position with the adaptor tube that indicates that the dental vacuum system useful vacuum is greater than about 7.25 SCFM and 4.6 inches Hg.

8. A dental vacuum assembly comprising:

a dental vacuum system for drawing a vacuum useful for dental purposes;

at least one dental vacuum system high volume evacuator valve or hose connected to said dental vacuum system so that air is drawn into said valve or hose;

an adaptor tube having a first open end and a second end, a constant cross-sectional area and configuration interior surface, and an external surface at at least said first end tightly fit with said dental vacuum system high volume evacuator valve or hose, and having a testing opening; and a vacuum indicating weight movably positioned to cooperate with said testing opening, said weight configured and dimensioned to, once moved into a position cooperating with said testing opening, remain in a position cooperating with said testing opening when the useful vacuum drawn by said vacuum system is at or above a level considered sufficient, and move away from said testing opening when the useful vacuum drawn by said vacuum system is at or below a level considered insufficient.

9. A dental vacuum assembly as recited in claim 8 wherein said testing opening comprises at least one opening in said external surface of said adaptor tube through which air can flow from exterior of said adaptor tube through said testing opening and then through said first open end; and wherein said vacuum indicating weight comprises a body portion which is mounted for movement between a first position covering said at least one opening in said external surface of said adaptor tube, and a second position not covering said at least one opening.

10. A dental vacuum assembly as recited in claim 9 wherein said vacuum indicating weight comprises a tube which slides over said external surface of said adaptor tube.

11. A dental vacuum assembly as recited in claim 9 wherein said adaptor tube second end is open and wherein said external surface of said adaptor tube has at least one opening therein; and wherein said vacuum indicating weight is solid and dimensioned to completely cover said adaptor tube second open end.

12. A dental vacuum assembly as recited in claim 8 wherein said adaptor tube second end is open, and wherein said vacuum indicating weight is tubular and has: a first portion with an exterior cross-section dimensioned and configured so that it fits within said adaptor tube-open second end so that airflow between said exterior cross section of said first portion and said adaptor tube is substantially precluded but there is no interference fits therebetween; a second portion with an exterior cross-section greater than that of said first portion and which will not fit within said adaptor tube open second end; and an internal passageway.

13. A dental vacuum assembly as recited in claim 12 wherein said first portion of said vacuum indicating weight has external indicia thereon indicating the desired amount of insertion thereof into said adaptor tube open second end.

14. A dental vacuum assembly as recited in claim 12 wherein said tubular vacuum indicating weight has a calibration element which modifies the mass or internal cross-section thereof.

15. A dental vacuum assembly as recited in claim 14 wherein said tubular vacuum indicating weight has a calibration element which modifies the mass or internal cross-section thereof.

16. A dental vacuum assembly as recited in claim 12 wherein said adaptor tube is made of plastic and said vacuum indicating weight is of stainless steel.

17. A dental vacuum assembly as recited in claim 16 wherein said adaptor tube has an internal surface defining a substantially circular cross-section having a diameter of about 0.4 inches, and wherein said adaptor tube external surface is substantially circular in cross section and has a diameter of about 0.42–0.44 inches at said first end thereof; and wherein said vacuum indicating weight first portion exterior has a substantially circular cross-section having a diameter of about 0.35–0.36 inches, and said vacuum indicating weight has a mass of about 23 grams.

18. A dental vacuum assembly as recited in claim 16 wherein said tubular vacuum indicating weight has a calibration element which modifies the mass or internal cross-section thereof.

19. A dental vacuum assembly as recited in claim 12 wherein said adaptor tube has an internal surface defining a substantially circular cross-section having a diameter of about 0.4 inches, and wherein said adaptor tube external surface is substantially circular in cross section and has a diameter of about 0.42–0.44 inches at said first end thereof; and wherein said vacuum indicating weight first portion exterior has a substantially circular cross-section having a diameter of about 0.35–0.36 inches, and said vacuum indicating weight has a mass of about 23 grams.

* * * * *